United States Patent [19]
Somack et al.

[11] Patent Number: 5,972,613
[45] Date of Patent: Oct. 26, 1999

[54] METHODS OF NUCLEIC ACID ISOLATION

[75] Inventors: Ralph Somack, Oakland; Stephen E. Moring, Moss Beach, both of Calif.

[73] Assignee: The Perkin-Elmer Corporation, Foster City, Calif.

[21] Appl. No.: 08/987,329

[22] Filed: Dec. 9, 1997

[51] Int. Cl.$^6$ .............................. C12Q 1/68; C12N 15/10
[52] U.S. Cl. ............................ 435/6; 435/91.1; 435/803; 536/26.42
[58] Field of Search ............................... 435/6, 91.1, 803; 435/810; 536/23.1

[56] References Cited

U.S. PATENT DOCUMENTS

| | | | |
|---|---|---|---|
| 5,155,018 | 10/1992 | Gillespie et al. | 435/91 |
| 5,234,809 | 8/1993 | Boom et al. | 435/91.2 |
| 5,284,940 | 2/1994 | Lin et al. | 536/25.4 |
| 5,459,253 | 10/1995 | Wolin et al. | 536/25.42 |
| 5,482,834 | 1/1996 | Gillespie et al. | 435/6 |

FOREIGN PATENT DOCUMENTS

| | | |
|---|---|---|
| WO94/18156 | 8/1994 | WIPO . |
| WO97/05248 | 2/1997 | WIPO . |

OTHER PUBLICATIONS

Zolfaghari et al. *Clin. Chem.* 39 (7), 1408–1411 (1993).
Cox et al., "The Isolation, Characterization and Acid–Base Properties of Ribonucleic Acid from Rabbit–Reticulocyte Ribosomes," *Biochem. J.* 89:574–585 (1963).
Cox et al., "Ribonucleic Acid from Ribonucleoprotein Particles," *Biochem. J.* 11:104–109 (1966).
MacDonald et al., "Isolation of RNA Using Guanidinium Salts," *Methods in Enzymology* 152:219–227 (1987).
Reichmann et al., "Preparation of Infectious Ribonucleic Acid from Potato Virus X by Means of Guanidine Denaturation," *Virology* 9:710–712 (1959).
Sela et al., "The Correlation of Ribonuclease Activity with Specific Aspects of Tertiary Structure," *Biochimica et Biophysica Acta* 26:502–512 (1957).
Zolfaghari et al., "Simple method for extracting RNA from cultured cells and tissue with guanidine salts," *Clin. Chem.* 39(7):1408–1411 (Abstract Only)(Jul., 1993).
Cathala et al., "Laboratory Methods, A Method for Isolation of Intact, Translationally Active Ribonucleic Acid," *DNA* 2(4):329–335 (1983).
Krawetz et al., "Isolation and Fractionation of Total Nucleic Acids from Tissues and Cells," *Journal of Biochemical and Biophysical Methods* 12:29–36 (1986).

*Primary Examiner*—John L. LeGuyader
*Assistant Examiner*—Mark L. Shibuya
*Attorney, Agent, or Firm*—Scott R. Bortner

[57] ABSTRACT

The invention relates to new methods of RNA isolation that exploit the surprising discovery that RNA may be differentially precipitated from DNA. The subject methods result in the formation of an RNA-containing precipitate that has an RNA content at least two fold enriched with respect to DNA, as compared with the RNA to DNA ratio of the solution from which the RNA-containing precipitate is derived. The invention also includes various methods of DNA isolation that employ the selective precipitation of RNA. The degree of RNA enrichment achieved is often much greater than two fold; enrichment by a factor of ten or greater is frequently obtained. By precipitating RNA from a solution, the RNA may be collected by simple procedures such as centrifugation or filtration, thereby avoiding the need to bind the RNA to solid phase. The collected RNA precipitate may then be solubilized. One embodiment of the subject methods involves forming an RNA-containing nucleic acid composition, adding an RNA precipitate forming chaotropic salt to the nucleic acid composition in a sufficient concentration to form an RNA-containing precipitate, collecting the RNA-containing precipitate, and (optionally) solubilizing the precipitate. Preferred precipitate forming chaotropic salts are guanidine hydrochloride and guanidine thiocyanate. Other embodiments of the invention include kits for performing the methods of the invention. The invention also includes systems for performing the methods of the invention.

18 Claims, No Drawings

METHODS OF NUCLEIC ACID ISOLATION

BACKGROUND

The preparation of relatively pure samples of nucleic acids such as DNA or RNA is an important step in many molecular biology procedures. Purification is necessary to ensure removal of impurities, e.g., cellular debris, that may interfere with subsequent molecular biological procedures. RNA purification has many uses such as in the preparation of cDNA and the monitoring of gene expression. While the purification of DNA from many types of cells is relatively straight forward, RNA purification is often problematic. Such difficulties include the need to inactivate ubiquitous RNA degrading enzymes and the lability of RNA in alkaline pH environments. Another difficulty with RNA purification is the frequent co-purification of RNA and DNA. Contaminating DNA may interfere with subsequent molecular biochemical or genetic analysis procedures because of the similar base pairing properties of DNA and RNA. Similarly, RNA may contaminate DNA preparations.

Numerous procedures have been developed for purifying RNA. These previously available RNA procedures suffer from one or more shortcomings such as the need for highly toxic chemicals, the use of an inconveniently large number of manipulations, genomic DNA contamination, a requirement for ultracentrifugation, the use of DNAses, RNAses, proteinase digestions, and contamination with inhibitors of genetic analysis procedures (e.g., PCR and base sequencing). Such RNA isolation methods usually include the cumbersome steps of adsorbing nucleic acids to a solid phase support and subsequently preferentially eluting the nucleic acid from the supports. Similar problems arise with previously available techniques for DNA isolation. Accordingly, it is of interest to provide new and improved methods of RNA and DNA purification. Ideally, such new methods are simple to perform and may easily be automated.

SUMMARY

The invention relates to new methods of RNA and DNA isolation that exploit the surprising discovery that RNA may be differentially precipitated from DNA in essentially a single step. The subject methods result in the formation of an RNA-containing precipitate that has a RNA content at least two fold enriched with respect to DNA, as compared with the RNA to DNA ratio of the solution from which the RNA-containing precipitate is derived. The degree of RNA enrichment achieved is often much greater than two fold; enrichment by a factor of one hundred or greater is frequently obtained. By precipitating RNA from a solution, the RNA may be collected by simple physical procedures such as centrifugation or filtration, thereby avoiding the need to bind the RNA to a solid phase or to employ enzymatic degradation. The collected RNA precipitate may then be solubilized.

One embodiment of the subject methods involves forming an RNA-containing nucleic acid composition, adding an RNA precipitate forming chaotropic salt to the nucleic acid composition in a sufficient concentration to form an RNA-containing precipitate, collecting the RNA-containing precipitate, and (optionally) solubilizing the precipitate. Preferred precipitate-forming chaotropic salts are guanidine hydrochloride and guanidine thiocyanate; guanidine hydrochloride is particularly preferred.

The step of forming the RNA-containing precipitate preferably takes place in a temperature range of 1° C.–25° C., more preferably in the range of 4° C.–10° C. Typically, although not necessarily, the precipitate forming step is performed for at least one hour.

Other embodiments of the invention include methods of isolating DNA. The subject DNA isolation methods employ a differential RNA precipitation step of the invention that may be used to isolate RNA by forming an RNA-containing precipitate, DNA remains in solution, thereby resulting in the purification of DNA with respect to RNA. The process of collecting the RNA results in the formation of an RNA depleted solution. DNA may then be precipitated from the RNA depleted solution by adding a nucleic acid precipitating agent, e.g., ethanol.

Other embodiments of the invention include kits for performing the methods of the invention. The invention also includes systems for performing the methods of the invention. The systems for RNA isolation comprise a cell lysis chamber, a precipitate collector, and a port for the introduction of a chaotropic salt.

SPECIFIC EMBODIMENTS OF THE INVENTION

The invention relates to new methods of RNA isolation that exploit the surprising discovery that RNA may be differentially precipitated from DNA. Thus the subject methods may be viewed not only as method of purifying RNA, but as a methods of separating RNA from DNA. Accordingly, the invention also provides for methods of isolating DNA. The subject methods may be used to purify many different forms of RNA, including messenger RNA (mRNA), ribosomal RNA (rRNA), and nuclear RNA. Similarly, the invention may be used to purify essentially all forms of DNA. The subject methods result in the formation of an RNA-containing precipitate that has a RNA content at least two fold enriched with respect to DNA, as compared with RNA/DNA ratio of the solution from which the RNA precipitate is derived. The degree of RNA enrichment achieved is often much greater than two fold. The RNA may be collected by simple procedures such as centrifugation or filtration, thereby avoiding the need to bind the RNA to solid phase. The collected RNA precipitate may then be solubilized. Thus not only do embodiments of the invention provide for the selective precipitation of RNA, but cumbersome additional steps such as phenol/chloroform extraction or adding agents, e.g., ethanol, to enhance adsorption to a solid support are unnecessary.

The term "isolation" as used herein with respect to nucleic acids (RNA or DNA) refers to methods of producing a composition that is of sufficient purity to serve as templates for primer extension in a polymerase catalyzed reaction such as PCR (the polymerase chain reaction) or cDNA generation. The purity of a nucleic acid containing composition may be ascertained, by among other methods, spectrophotometrically by measuring the $A_{260}/A_{280}$ absorption ratio. This ratio is indicative of the amount of nucleic acid and protein in a composition. Preferably, the $A_{260}/A_{280}$ of the purified nucleic acid of interest is at least 1.8, more preferably, at least 2.0. Nucleic acid containing compositions that have been produced by the subject RNA and DNA preparation methods are said to be "purified." An RNA-containing precipitate formed by a method of the invention is said to be purified RNA. RNA-containing precipitates formed by the methods of the invention may include various components other than RNA. Such additional components include (in relatively minute amounts) counter-ions, proteins, DNA, and the like.

The RNA-containing precipitates formed by the method of the invention are particularly advantageous because the subject methods preferentially precipitate RNA rather than DNA. This differential precipitation effect is quite surprising given the chemical similarity between RNA and DNA. Many methods of RNA purification require special steps to remove DNA contaminating an RNA preparation, e.g., the addition of DNAses. The RNA-containing precipitates formed by the methods of the invention show at least two-fold enrichment with respect to the RNA/DNA ratio in the nucleic acid containing composition from which the RNA-containing precipitate is formed. In most embodiments of the subject method, the degree of RNA enrichment relative to DNA found in the RNA-containing precipitate is significantly higher than two fold. RNA enrichments of at least one hundred fold may be achieved in most embodiments.

The methods of the invention may be applied to isolate RNA from most RNA-containing material. Examples of potential sources include tissue culture samples, biological preparations (including plant tissue homogenates) and patient samples, e.g., blood, saliva, semen, spinal fluid, biopsy samples, and the like. RNA-containing compositions may be obtained by lysing cells (or viruses) or by collecting nucleic acids that have already been released into an environment of interest. Nucleic acid-containing compositions may be obtained by lysing either prokaryotic or eukaryotic cells. Cells may be concentrated prior to lysis, e.g., by centrifugation or filtration. Cells may be lysed by a variety of methods useful for lysing cells in conventional nucleic acid preparation techniques. Methods of forming cellular lysates for nucleic acid isolation are well known and can be found, among other places, in Sambrook et al., Molecular Cloning Methods, ColdSpring Harbor Press, ColdSpring Harbor, N.Y. (1989) and Jones et al., RNA Isolation and Analysis, BIOS Scientific Publishers, Oxford (1994). Such lysis methods include, but are not limited to, detergents, washing, enzyme treatment, enzymes and sonication. In a preferred embodiment of the invention, lysis is effected through the addition of a lysis solution comprising a guanidine salt and a non-ionic detergent, Tween-20 being particularly preferred as the non-ionic detergent. The addition of a chaotropic salt may be used for cell lysis and the formation of an RNA-containing precipitate in the same step.

Chaotropic salts are used to form an RNA-containing precipitate. The term chaotropic salt refers to a substance capable of altering the secondary or tertiary structure of a protein or nucleic acid, but not altering the primary structure of the protein or nucleic acid. Examples of chaotropic salts include, but are not limited to, guanidine thiocyanate, guanidine hydrochloride sodium iodide, potassium iodide, sodium isothiocyanate, urea. Guanidine salts other than guanidine thiocyanate and guanidine hydrochloride may be used as a chaotropic salts in the subject methods. Not all chaotropic salts are capable of eliciting the formation of an RNA-containing precipitate from an RNA-containing preparation. Those chaotropic salts that are capable of eliciting the formation of an RNA-containing precipitate may, for the sake of convenience, be referred to as "RNA precipitate forming chaotropic salts." RNA precipitate forming chaotropic salts may be identified by using routine experimentation of chaotropic salts of interest for the ability to elicit RNA-containing precipitate formation, e.g., adding a chaotropic salt to a solution known to contain RNA and monitoring for RNA-containing precipitate formation. Preferred chaotropic salts for use in the subject methods are guanidine hydrochloride and guanidine thiocyanate, guanidine hydrochloride being particularly preferred. The concentration of chaotropic salt used to elicit RNA-containing precipitant formation may vary in accordance with the specific chaotropic salt selected. Factors such as the solubility of the specific salt must be taken into account. Routine experimentation may be used in order to determine suitable concentration of chaotropic salt for eliciting RNA-containing precipitate formation. In embodiments of the invention employing guanidine hydrochloride as the chaotropic salt, the concentration of guanidine hydrochloride in the nucleic acid containing solution from which the RNA-containing precipitate is obtained is in the range of 1 M to 3 M, 2 M being particularly preferred. In embodiments of the invention employing guanidine thiocyanate as the chaotropic salt, the concentration of guanidine thiocyanate in the nucleic acid-containing solution from which the RNA-containing precipitate is obtained is in the range of 0.5 M to 2 M, 1 M being particularly preferred. Combinations of chaotropic salts may be used to elicit RNA-containing precipitate formation. In embodiments of the invention employing multiple chaotropic salts, the chaotropic salts may be added in the form of concentrated solution or as a solid (and dissolved in the initial RNA-containing preparation).

After the addition of the chaotropic salts, the solution is allowed to incubate for a period of time sufficient to permit an RNA-containing precipitate to form. Unless the incubation conditions are modified during incubation, e.g., a temperature change, the longer the period of incubation time, the larger the quantity of RNA precipitate that will form. Incubation preferably occurs under constant temperature conditions. When a sufficient quantity of RNA precipitate for the purpose of interest, e.g., cDNA library formation, is formed, the RNA precipitate may be collected. The quantity of RNA precipitate formed may be monitored during incubation. Monitoring may be achieved by many methods, such methods include visually observing the formation of the precipitate (e.g., visually), collecting the precipitate during the incubation process and the like. In most embodiments of the invention, incubation time is at least one hour, preferably incubation is at least eight hours. Periods for incubation may be considerably longer than eight hours; no upper limit for incubation time is contemplated although need to obtain isolated RNA in a reasonable amount of time may be a constraint.

The temperature of the mixture formed by adding the chaotropic salt to the RNA-containing composition of interest, e.g., a cell lysate, influences the amount of RNA-containing precipitate formed in the subject method. In general, a greater precipitate yield will be obtained at a lower temperature, i.e., below room temperature. Preferably, freezing is avoided; however, a RNA-containing precipitate may form if a fresh cellular lysate is rapidly frozen. Additionally, lower temperatures may be used to reduce the activity of RNAses or detrimental chemical reactions occurring in the processed sample. Preferably, the temperature of the solution from which the RNA-containing precipitate formed is in the range of 1° C. to 25° C., more preferably in the range of 4° C. to 10° C.

After the RNA-containing precipitate has formed, the RNA-containing precipitate is collected. Collection entails the removal of the RNA-containing precipitate from the solution from which the precipitate was formed. The precipitate may be separated from the solution by any of the well known methods for separation of a solid phase from a liquid phase. For example, the RNA-containing precipitate may be recovered by filtration or centrifugation. Many types of filtration and centrifugation systems may be used to collect the RNA-containing precipitate. Precautions against RNA degradation should be taken during the RNA precipitate collection step, e.g., the use of RNAase-free filters and tubes, reduced temperatures.

After the RNA-containing precipitate has been recovered, the precipitate may optionally be washed so as to remove remaining contaminants. A variety of wash solutions may be used. Wash solutions and washing conditions should be designed so as to minimize RNA losses from the RNA-containing precipitate. Preferably a wash solution containing the same chaotropic salt used to form the RNA-containing precipitate is used to wash the collected RNA-containing precipitate. The concentration of the chaotropic salt in the wash solution is preferably high enough for an RNA-containing precipitate to form, thereby minimizing losses of the RNA-containing precipitate during the washing process. Additionally, the washing solution is preferably at a temperature sufficiently low for RNA-containing precipitates to form, thereby minimizing losses of the RNA-containing precipitate during the washing process.

The collected RNA-containing precipitate may be solubilized so as to enable subsequent manipulation of the purified RNA in solutions. Solubilization may be accomplished by contacting the collected RNA-containing precipitate with a solution that does not elicit the formation of an RNA-containing precipitate. Typically, such a solution is an aqueous buffer (low ionic strength) or water. Examples of such buffers includes 10 mM Tris-HCl (pH 7.0), 0.1 mM EDTA; suitable buffering agents include, but are not limited to, tris, phosphate, acetate, citrate, glycine, pyrophosphate, aminomethyl propanol, and the like. The RNA-containing precipitate and the solution may be actively mixed, e.g., by vortexing, in order to expedite the solubilization process.

It will readily be appreciated by persons skilled in the art that DNA may be isolated from a nucleic acid containing solution (containing both DNA and RNA) by forming an RNA-containing precipitate in accordance with the methods of the invention. An RNA depleted solution is produced as a necessary consequence of forming an RNA-containing precipitate from a solution comprising DNA and RNA. DNA may be isolated from the RNA depleted solution by adding a nucleic acid precipitating agent. Nucleic acid precipitating agents for use in the subject methods are capable of precipitating DNA from a DNA-containing solution. Nucleic acid precipitating agents for use in the subject methods may also be capable of precipitating RNA. Compounds capable of precipitating RNA and DNA are well known and include many alcoholic compounds, concentrated ethanol being particularly preferred. The DNA precipitate may then be collected (in the same manner as an RNA-containing precipitate), optionally washed, and solubilized. The RNA-containing precipitates formed may or may not be saved for analysis.

Embodiments of the invention include systems for performing the subject methods of RNA isolation. In one embodiment of the systems, the systems comprise a cell lysis chamber, a precipitate collector, a port for introduction of a chaotropic salt that can be used to form a RNA-containing precipitate in accordance with the subject methods. The components of the systems of the invention cooperate so as to enable the performance of one or more embodiments of the subject methods of RNA isolation. The various components of the RNA isolation systems of the invention may or may not be portions of a unitary device or apparatus. The cell lysis chamber may be used to contain a cell lysate. The cell lysate may be formed in the cell lysate chamber (after the introduction of cells and lysis solution) or the cell lysate may be introduced directly into the cell lysate chamber. The port for the introduction of the chaotropic salt is configured so as to cooperate with the cell lysis chamber in order to permit the introduction (either in dry form or as a solution) of the chaotropic salt into the chamber. Embodiments of the system may comprise a reservoir of chaotropic salt for introduction into the lysis chamber. The reservoir and the entry port may or may not be the same structure. The precipitate collector serves to collect a RNA-containing precipitate formed by the addition of the chaotropic salt. The collector may take on many forms, such forms include a filter. Filters may or may not be removable.

Other embodiments of the invention include kits for performing the subject nucleic acid isolation methods. Kits serve to expedite the performance of the subject methods by providing multiple reagents packaged together. Reagents may be supplied in pre-measured units so as to increase precision and reliability of the methods. Kits preferably contain detailed instructions for practicing one or more embodiments of the subject nucleic acid preparation methods. The kits of the invention comprise cell lysis buffer containing a chaotropic salt, a buffer for washing RNA-containing precipitates, and a buffer for solubilizing RNA-containing precipitates (formed by the subject methods). The kits may optimally comprise a precipitate collector, e.g., a filtration device.

The invention, having been described above, may be better understood by reference to the following examples. The following examples are offered for purposes of illustrating the invention and should not be construed as limitations on the invention.

EXAMPLES

Example 1

Centrifugation Protocol for Purification of Total RNA from Cultured Cells

1. Lysis and Centrifugation
a. Add 100 $\mu$L of Cell Lysate Solution (containing, 4M guanidine HCl, 300 mM MES, pH 6.0, 400 mM NaCl and 5% Tween 20) to a sample tube, containing cell suspension in 100 $\mu$l of PBS buffer solution.
b. Mix the sample by pumping 3–5 times with pipette action through a 200 $\mu$l pipetteman tip (set at 175 $\mu$l). Cover tubes and allow to stand at ambient temperature for 10 minutes. Incubate at 4° C. on ice for a minimum of one hour.
c. Allow lysates to come to 22–25° C. Shear DNA by pumping lysate 10–15 times through a 200 $\mu$l tip.
e. Centrifuge sample tube at 10,000 rpm (~6000×g) for 10 minutes. Discard supernatant. Note, the supernatenis can be used to recover genomic DNA.
2. Purification Wash
a. Add 500 $\mu$l of Wash Solution I (2M guanidine HCl, 200 mM NaCl, 150 mM MES, pH 6.0) to the centrifuge tube, and resuspend pellet by vortexing for 5 seconds.
b. Centrifuge sample tube at 10,000 rpm (~6000×g) for 10 minutes. Discard supernatant.
3. Final Wash
a. Add 500 1 of Wash Solution II (20 mM Tris-HCl, pH 8.0, 200 mM NaCl in DEPC treated $H_2O$ plus absolute ethanol to a final concentration 70% V/V) to the centrifuge tube, and resuspend pellet by vortexing for 5 seconds.
b. Centrifuge sample tube at 10,000 rpm (~6000×g) for 10 minutes. Discard supernatant.
c. Repeat steps 3a and 3b.
d. Remove all liquid above the pellet and air dry at 55° C. for 5 minutes.

4. Solubilization of RNA
a. Add 100 to 200 μl of DEPC water to tube containing pellet and vortex for 5 seconds. Allow to stand at ambient temperature for 2 to 5 minutes.
b. Place tubes immediately on ice or store at −80° C.

5. Recovery of Genomic DNA from Lysate Supernatant
DNA precipitation
a. Add 40 μl of 5M NaCl solution to the supernatant from step 1 e and mix by vortexing for 1 second.
b. Add 400 μl of absolute ethanol and mix by vortexing (total volume 640 μl). Allow to stand at room temperature for 10 minutes.
c. Centrifuge sample tube at 10,000 rpm (~6000×g) for 10 minutes. Discard supernatant.

Wash
d. Resuspend pellet in 500 μL of a solution of 20 mM Tris-HCl, pH 8.0, 200 mM NaCl in DEPC treated $H_2O$ plus absolute ethanol to a final concentration 70% V/V. Vortex tube for 2–4 seconds.
e. Centrifuge sample tube at 10,000 rpm (~6000×g) for 10 minutes. Discard supernatant.
f. Repeat steps d and e.
g. Remove all liquid above the pellet and air dry at 55° C. for 5 minutes.

Solubilization of DNA
h. Add 100 to 200 μl of a solution 10 mM Tris-HCl, 0.1 mM EDTA, pH 8.0 to tube containing pellet and vortex for 5 seconds. Incubate at 40° C. for 10 minutes and vortex for 5 seconds.
i. Place tubes on ice or store at −15° C.

Example 2

Protocol for Purification of Total RNA and DNA from Cultured Cells and Tissues with Purification Tray Columns A. RNA Purification
1. Nucleic Acid Filtration
a. From cell suspensions Add 100 μL of Cell Lysis Solution (containing, 4M guanidine-HCl, 300 mM MES, pH 6.0, 400 mM NaCl and 2% Tween 20) to a sample tube, containing cell suspension in 100 μl of PBS buffer solution. From cell culture plates with adherent cells Add 100 μl of Cell Lysis Solution to individual wells in a 96 well cell culture plate with the culture media removed. From animal tissues Excise 1 to 3 mg of tissue and wash in PBS buffer. Place tissue into a micro homogination tube. Add 100 μl of Cell Lysate Solution and homogenize with motor driven pistle for 30 seconds. Allow homogenate to stand at ambient temperature for 10 minutes. Remove the upper 50 μl of the homogenate suspension with care not to include any particulate cellular debries. Place the clear homogenate into a clean sample tube and dilute with 50 μl of PBS or RNase free water. Mix the samples by pumping 3–5 times with pipette action. Incubate at 4° C. for one hour. Skip to step 1C.
b. Mix the samples by pumping 3–5 times with pipette action through a 200 μl pipetteman tip (set at 175 μl). Cover tubes and allow to stand at ambient temperature for 10 minutes. For cell control lysates and cell suspension lysates: Incubate at 4° C. for one hour. For cell culture plate lysates: Dilute the lysate by the addition of 100 μl of Elution Buffer and mix the samples by pumping 3–5 times with pipette action. Incubate at 4° C. for one hour.
c. Pre-wet tray filters: To selected wells of a 96 Well Purification Tray, add 50 μL of Wash Buffer I (see 2 below). Allow the solution to permeate the tray filters for 5 minutes.
d. Shear DNA by pumping lysate 10 to 15 times through a 200 μl tip.
e. Transfer lysate mixture to tray wells. Apply vacuum at 8–10 inches Hg to column tray and filter at a rate of 1 drop/3–5 seconds until air passes through the filters. Collect flow-through in a suitable 96 well sample tray if DNA is to be recovered for later purification.

2. Purification Wash
a. Flush tray wells once with 400 μl of Wash Solution I (2M guanidine HCl, 200 mM NaCl, 150 mM MES, pH 6.0). Apply vacuum at 8–10 inches Hg until air passes through the filters.

3. Final Wash
a. Flush tray wells with 500 μL of RNA Wash Solution II (20 mM Tris-HCl, pH 8.0, 200 mM NaCl in DEPC treated $H_2O$ plus absolute ethanol to a final concentration 70% V/V). Take care to rinse the sides of the wells.
b. Wash the tray wells twice with 300 μL of RNA Wash Solution II. Discard the flow-through (filtrate).
c. Purge tray wells with 30 ml of air (or 30 seconds) to remove residual ethanol.

4. Elution of RNA
a. Place purification tray on top of a 96 well PCR tray (sample archive tray).
b. Add 150 μl of Elution Solution (0.1 mM EDTA, 0.01% sodium azide) to the top of the purification tray filters. Incubate at 20–25° C. for 5 minutes.
c. Flush into collection tubes (MicroAmp wells) under vacuum at 2–4 inches until liquid meets the top of all the tray filter membranes.
d. Increase the vaccum to 10 inches of Hg for 5 to 10 seconds.
e. Place tubes immediately on ice or store at −80° C.

B. DNA Purification
1. DNA Precipitation and Filtration
From a Cell Lysate Filtrate collected in the total RNA purification protocol:
a. Add 40 μl of 5M NaCl solution to lysate filtrate and mix by pumping 3–5 times with pipette action through a 200 μl pipetteman tip (set at 200 μl).
b. Add 300 μl of absolute ethanol and mix by pipette action (total volume; 550 μl).
c. Pre-wet purification tray filters: To selected wells of a second 96 well filter purification tray, add 50 μL of Wash Buffer II (see 2a below). Allow the solution to permeate the purification tray filters.
d. Transfer lysate mixture to purification tray wells. Apply vacuum at 8–10 inches Hg to tray and filter at a rate of 1 drop/3–5 seconds until air passes through the filters. Discard flow-through (Vent to waste).

2. Wash
a. Flush purification tray wells with 500 μL of Wash Solution II (20 mM Tris-HCl, pH 8.0, 200 mM NaCl in DEPC treated $H_2O$ plus absolute ethanol to a final concentration 70% V/V). Take care to rinse the sides of the wells.
b. Wash the tray wells twice with 300 μL of Wash Solution II. Discard the flow-through (filtrate).
c. Purge tray wells with 30 ml of air (or 30 seconds) to remove residual ethanol.

3. Elution of DNA
a. Place purification tray on top of a 96 well PRC tray (or 200 μl collection tray).
b. Add 150 μl of Elution Solution (0.1 mM EDTA, 0.01% sodium azide) to column membrane. Incubate at 50° C. for 5 minutes.
c. Flush into a 96 well PRC tray under vacuum at 2–4 inches until liquid meets the top of all the tray filter membranes.

9 d. Increase the vacuum to 10 inches of Hg for 5 to 10 seconds. Store sample tray at 4 to 8° C.

Example 3

Protocol for Purification of Total RNA and DNA from Cultured Cells and Tissues with Spin Columns A. RNA Purification 1. Nucleic Acid Filtration a. From cell suspensions Add 100 μL of Cell Lysis Solution (containing, 4M guanidine-HCl, 300 mM MES, pH 6.0, 400 mM NaCl and 2% Tween 20) to a sample tube, containing cell suspension in 100 μl of PBS buffer solution. From cell culture plates with adherent cells Add 100 μl of Cell Lysis Solution to individual wells in a 96 well cell culture plate with the culture media removed. From animal tissues Excise 1–3 mg of tissue and wash in PBS buffer. Place tissue into a micro homogenization tube. Add 100 μl of Cell Lysate Solution and homogenize with motor driven pistil for 30 seconds. Allow homogenate to stand at ambient temperature for 10 minutes. Remove the upper 50 μl of the homogenate suspension with care not to include any particulate cellular debris. Place the clear homogenate into a clean sample tube and dilute with 50 μl of PBS or RNase free water. Mix the samples by pumping 3–5 times with pipette action. Incubate at 4° C. for a minimum of one hour. Skip to step 1C.

b. Mix the samples by pumping 3–5 times with pipette action through a 200 μl pipetteman tip (set at 175 μl). Cover tubes and allow to stand at ambient temperature for 10 minutes. For cell suspension lysates: Incubate at 4° C. for a minimum of one hour. For cell culture plate lysates: Dilute the lysate by the addition of 100 μl of Elution Buffer (see step 4a, below) and mix the samples by pumping 3–5 times with pipette action. Incubate at 4° C. for a minimum of one hour.

c. Pre-wet spin column filters: Add 50 μl of Wash Buffer I (see 2 below). Allow the solution to permeate the column filters for 5 minutes.

d. Shear DNA by pumping lysate 10–15 times through a 200 μl tip.

e. Transfer lysate mixture to spin column wells. Centrifuge at 2000 rpm for 60 seconds. Transfer the spin column insert to a clean collection tube. Save the collection tube containing the cell lysate filtrate if DNA is to be recovered from sample.

2. Purification Wash Add 500 μl of Wash Solution I (2M guanidine HCl, 200 mM NaCl, 150 mM MES, pH 6.0) to the spin column. Centrifuge at 2000 rpm for 2 minutes. Remove and discard the filtrate (flow through). Repeat step with the addition of 500 μl of Wash Solution I. Replace the column insert into the collection tube.

3. Final Wash a. Add 500 μL of Wash Solution II (20 mM Tris-HCl, pH 8.0, 200 mM NaCl in DEPC treated $H_2O$ plus absolute ethanol to a final concentration 70% V/V). To the spin column Take care to rinse the sides of the insert. Centrifuge at 2000 rpm for 2 minutes and filtrate.

b. Repeat the above step twice with the addition of 500 μL of Wash Solution II and centrifugation at 2000 rpm for 2 minutes. Centrifuge at 8000 rpm for an additional minute. Discard the filtrate.

c. Transfer the spin column insert to a clean collection tube.

4. Elution of RNA a. Add 200 μl of Elution Solution (0.1 mM EDTA, 0.01% sodium azide) to the spin columns. Incubate at 20–25° C. for 5 minutes.

10 b. Centrifuge (total volume 640 μl) into collection tubes at 4000 rpm for 60 seconds.

c. Remove and discard spin column insert. Place collection tubes immediately on ice or store at −80° C.

B. DNA purification

1. DNA Precipitation and Filtration

From a Cell Lysate Filtrate collected in the total RNA purification protocol:

a. Add 40 μl of 5M NaCl solution to lysate filtrate and mix by pumping 3–5 times with pipette action through a 200 μl pipetteman tip (set at 200 μl).

b. Add 400 μl of absolute ethanol and mix by pipette action (total volume; 640 μl).

c. Pre-wet spin column filters. Add 30 μL of Wash Buffer II to the filter membrane of a spin column insert (see 2a below). Allow the solution to permeate the filters.

d. Transfer lysate mixture to the spin-column insert. Centrifuge at 2000 rpm for 60 seconds.

Discard flow-through (filtrate). Aspirate contents of collection tube and re-use.

2. Wash a. Add 500 μL to the spin-column inserts with Wash Solution II. Take care to rinse the sides of the wells. Centrifuge at 2000 rpm for 2 minutes and discard the flow-through.

b. Repeat step "a" twice with the addition of 500 μl of Wash Solution II.

c. Centrifuge at 8000 rpm for an additional 60 seconds to remove residual ethanol.

3. Elution of DNA a. Replace the spin column collection tubes with clean tubes.

b. Add 200 μl of heated (at 70° C. TBE buffer to column inserts). Incubate at 50° C. for 5 minutes.

c. Centrifuge the spin columns at 2000 rpm for 2 minutes.

d. Remove and discard inserts and store collection tube at 4–8° C. or freeze and store at −15° C.

Incorporation by Reference

All papers and documents (including patents) referenced in this specification are incorporated herein by reference.

Equivalents

While the invention has been described with reference to specific methods and embodiments, it will be appreciated that various modifications and changes may be made without departing from the invention. These and other equivalents are intended to be covered by the following claims.

What is claimed is:

1. A method of isolating RNA from a nucleic acid composition comprising RNA and DNA, said method comprising the steps, forming an RNA-containing precipitate from the nucleic acid composition, wherein the ratio of RNA to DNA in the RNA-containing precipitate is at least 2 fold higher than the ratio of RNA to DNA in the RNA in the nucleic acid composition and wherein the precipitate is formed independent of a filter or carrier particle, wherein the formation of the RNA-containing precipitate does not require the addition of ethanol, and collecting the RNA-containing precipitate, whereby an RNA depleted solution is produced.

2. The method according to claim 1, comprising the step of solubilizing the RNA-containing precipitate.

3. The method according to claim 1, wherein the step of forming the RNA-containing precipitate from the nucleic acid composition comprises the step of adding a chaotropic salt to the nucleic acid composition.

4. The method according to claim 3, wherein the chaotropic salt is selected from the group consisting of guanidine thiocyanate and guanidine hydrochloride.

5. The method according to claim 4, wherein the chaotropic salt is guanidine hydrochloride.

6. The method according to claim 4, wherein the concentration of the guanidine hydrochloride in the nucleic acid composition is in the range of 1 M to 3 M.

7. The method according to claim 4, wherein the chaotropic salt is guanidine thiocyanate.

8. The method according to claim 7, wherein the concentration of the guanidine thiocyanate in the nucleic acid composition is in the range of 0.5 M to 2M.

9. The method according to claim 1, wherein the nucleic acid composition comprising DNA and RNA is formed by lysing a cell.

10. The method of claim 9, wherein the step of cell lysis comprises adding a detergent.

11. The method according to claim 9, wherein the detergent is a non-ionic detergent.

12. The method of claim 11, where the non-ionic detergent is TWEEN 20.

13. The method according to claim 3, wherein the nucleic acid containing composition is incubated at a temperature in the range of 4–25° C. for a period of time sufficient to produce the RNA-containing precipitate.

14. The method according to claim 13, wherein the period of time is one hour or less.

15. The method according to claim 1, wherein the RNA-containing precipitate is collected by a method selected from the group consisting of filtration, centrifugation, and gravimetric settling.

16. A method of isolating DNA from an RNA-depleted solution, comprising forming an RNA-depleted solution, wherein the RNA-depleted solution is prepared by forming an RNA-containing precipitate from a nucleic acid composition comprising RNA and DNA, wherein the ratio of RNA to DNA in the RNA-containing precipitate is at least 2 fold higher tan the ratio of RNA to DNA in the RNA in the nucleic acid composition and wherein the precipitate is formed independent of a filter or carrier particle, wherein the formation of the RNA-containing precipitate does not require the addition of ethanol, collecting the RNA-containing precipitate, whereby the RNA depleted solution is produced, adding a nucleic acid precipitating agent to the RNA depleted solution, whereby a DNA-containing precipitate is formed, and collecting the DNA-containing precipitate.

17. The method according to claim 16, wherein the nucleic acid precipitating agent is ethanol.

18. The method according to claim 16, wherein the chaotropic salt is selected from the group consisting of guanidine thiocyanate and guanidine hydrochloride.

\* \* \* \* \*